United States Patent
Wang et al.

(10) Patent No.: US 8,247,529 B2
(45) Date of Patent: Aug. 21, 2012

(54) NEOPLASIA TARGETING PEPTIDES AND METHODS OF USING THE SAME

(75) Inventors: Thomas D. Wang, Ann Arbor, MI (US); Shaoying Lu, Redwood City, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 483 days.

(21) Appl. No.: 12/466,942

(22) Filed: May 15, 2009

(65) Prior Publication Data

US 2010/0061929 A1 Mar. 11, 2010

Related U.S. Application Data

(60) Provisional application No. 61/128,210, filed on May 19, 2008.

(51) Int. Cl.
*A61K 38/00* (2006.01)
*A61K 38/08* (2006.01)

(52) U.S. Cl. ......... 530/300; 530/329; 514/1.1; 514/21.7

(58) Field of Classification Search ........................ None
See application file for complete search history.

(56) References Cited

U.S. PATENT DOCUMENTS

| | | | | |
|---|---|---|---|---|
| 6,558,668 B2 * | 5/2003 | Liau | ........................ | 424/174.1 |
| 6,610,836 B1 * | 8/2003 | Breton et al. | ................. | 536/23.1 |
| 2002/0018767 A1 * | 2/2002 | Lee et al. | ................... | 424/93.21 |
| 2004/0031072 A1 * | 2/2004 | La Rosa et al. | ............... | 530/330 |
| 2007/0061916 A1 | 3/2007 | Kovalic et al. | | |

OTHER PUBLICATIONS

Microcin E492, a channel-forming beacteriocin from *Klebsiella pneumoniae*, induces apoptosis in some human cell lines, PNAS, vol. 99 No. 5, 2002.*
Li et al., "Affinity fluorescence-labeled peptides for the early detection of cancer in Barrett's esophagus" In:Proc. SPIE; Mar. 2, 2009; vol. 7172, 71720JI[online]: downloaded from: http://spiedl.aip.org/getabs/servlet/ on Oct. 19, 2009; Abstract Only.
Kim et al., "Complete Genome Sequence of *Leuconostoc citreum* KM20" In: J. Bacteriol. Apr. 2008; vol. 190, No. 8, p. 3093-3094.
Genbank Accession: YP_001728401.1 "EMAP domain-containing protein [*Leuconostoc citreum* KM20]"; Apr. 11, 2006; [online]; Retrieved on Oct. 13, 2009 from: http://www.ncbi.nlm.nih.gov/protein/170017482. pp. 2.
Hsuing et al., "Detection of colonic dyspiasia in vivo using a targeted heptapeptide and confocal microendoscopy" In: Nature Medicine Apr. 2008; Epub Mar. 16, 2008; vol. 14, No. 4, pp. 454-458.

* cited by examiner

*Primary Examiner* — Christina Bradley
*Assistant Examiner* — Jeanette Lieb
(74) *Attorney, Agent, or Firm* — Edward J. Baba; Bozicevic, Field & Francis LLP

(57) ABSTRACT

The present invention provides compositions including neoplasia targeting peptides as well as methods of using the neoplasia targeting peptides in diagnosing, detecting, treating, monitoring treatment, and analyzing cancer or cancer cells in vivo and in vitro.

18 Claims, 8 Drawing Sheets

NEOPLASIA TARGETING PEPTIDES AND METHODS OF USING THE SAME

CROSS-REFERENCE

This application claims the benefit of U.S. Provisional Application No. 61/128,210, filed May 19, 2008, which application is incorporated by reference in its entirety.

BACKGROUND OF THE INVENTION

Malignant tumors are among the greatest health problems of man as well as animals, being one of the most common causes of death, also among young individuals. Available methods of treatment of cancer are quite limited, despite intensive research efforts during several decades. Although curative treatment, usually surgery in combination with chemotherapy and/or radiotherapy, is sometimes possible, malignant tumors still require a huge number of lives every year. In fact, curative treatment is rarely accomplished if the disease is not diagnosed early. In addition, certain tumor types can rarely, if ever, be cured.

There are various reasons for this very undesirable situation, the most important one clearly being the fact that most treatment schedules, except surgery, lack sufficient selectivity. Chemotherapeutic agents commonly used do not act on the malignant cells of the tumors alone but are highly toxic to other cells as well, especially to rapidly dividing cell types, such as hematopoietic and epithelial cells, resulting in highly undesirable side effects. The same applies to radiotherapy.

Additionally, short circulation half-life in plasma, limited aqueous solubility, and non-selectivity are usually encountered by most of the currently available anticancer drugs and thus restrict their therapeutic efficacy (Adv. Drug Deliver. Rev. 2002;54:695-713). In addition, two major problems plague the non-surgical treatment of malignant solid tumors. Physiological barriers within tumors impede the delivery of therapeutics at effective concentrations to all cancer cells, and acquired drug resistance resulting from genetic and epigenetic mechanisms reduces the effectiveness of available drugs.

Also in the diagnosis of cancer and of metastases, including the follow-up of patients and the study of the effects of treatment on tumors and metastases, reliable, sensitive and more selective methods and agents would be a great advantage. All methods currently in use, such as nuclear magnetic resonance imaging, X-ray methods, histological staining methods still lack agents that are capable of targeting an entity for detection specifically or selectively to tumor tissues, metastases or tumor cells and/or to tumor endothelium.

Therefore, there is a continuing need in the art for new diagnostic and prognostic methods as well as methods and compositions to allow for cancer targeting and to improve management of patient care.

SUMMARY OF THE INVENTION

The present invention provides compositions including neoplasia targeting peptides as well as methods of using the neoplasia targeting peptides in diagnosing, detecting, treating, monitoring treatment, and analyzing cancer or cancer cells in vivo and in vitro.

A feature of the present invention is a composition including a polypeptide up to 50 amino acids in length and an amino acid sequence selected from ASYNYDA (SEQ ID NO:01), AQLSTLA (SEQ ID NO:02), QLMSADS (SEQ ID NO:03), LPLHSLS (SEQ ID NO:04), and TGPTIQH (SEQ ID NO:05). In some embodiments, the polypeptide is coupled to at least one effector molecule, such as a therapeutic agent, or a detectable molecule. In certain embodiments, the detectable molecule comprises a chelator, a complexed metal, an enriched isotope, radioactive material, a paramagnetic substance, an affinity label, a fluorescent label, a luminescent label, a PET-active substance or a SPECT-active substance. In some embodiments, the detectable molecule is fluorescein or a fluorescein derivative. In some embodiments, the detectable molecule is rhodamine or a rhodamine derivative. In some embodiments, the therapeutic agent is a cytotoxic agent, a cytostatic agent, an immunomodulating agent, or a radiation emitting agent. In certain embodiments, the therapeutic agent is a chemotherapeutic agent. Another feature of the present invention is a nucleic acid encoding the polypeptide.

Another feature is the present invention is a pharmaceutical composition including a polypeptide coupled to a therapeutic agent, wherein the polypeptide comprises up to 50 amino acids in length and an amino acid sequence selected from ASYNYDA (SEQ ID NO:01); AQLSTLA (SEQ ID NO:02); QLMSADS (SEQ ID NO:03); LPLHSLS (SEQ ID NO:04); and TGPTIQH (SEQ ID NO:05). In some embodiments, the composition further includes at least one of a pharmaceutically acceptable carrier, a pharmaceutically acceptable diluent, a pharmaceutically acceptable excipient and a pharmaceutically acceptable adjuvant. In some embodiments, the therapeutic agent is a cytotoxic agent, a cytostatic agent, an immunomodulating agent, or a radiation emitting agent. In certain embodiments, the therapeutic agent is a chemotherapeutic agent.

Another feature of the present invention is a method of detecting presence or absence of a tumor cell in a subject, by administering a composition comprising a polypeptide coupled to a detectable molecule to a subject, wherein the polypeptide comprises up to 50 amino acids in length and an amino acid sequence selected from ASYNYDA (SEQ ID NO:01), AQLSTLA (SEQ ID NO:02), QLMSADS (SEQ ID NO:03), LPLHSLS (SEQ ID NO:04), and TGPTIQH (SEQ ID NO:05), and wherein the polypeptide is capable of binding to a tumor cell; and detecting a level of binding of the polypeptide coupled to a detectable molecule in the subject as compared to a negative control, wherein an increase in binding of the polypeptide coupled to a detectable molecule as compared to a negative control indicates the presence of a tumor cell in the subject. In certain embodiments, the detectable molecule comprises a chelator, a complexed metal, an enriched isotope, radioactive material, a paramagnetic substance, an affinity label, a fluorescent label, a luminescent label, a PET-active substance or a SPECT-active substance. In some embodiments, the detectable molecule is fluorescein or a fluorescein derivative. In some embodiments, the detectable molecule is rhodamine or a rhodamine derivative. In some embodiments, the tumor cell is an adenocarcinoma cell, such as an esophageal cancel cell.

Another feature of the present invention is a method of delivering a therapeutic agent to a cancer cell in a subject, by administering a composition comprising a polypeptide coupled to a therapeutic agent to a subject in need thereof, wherein the polypeptide comprises up to 50 amino acids in length and an amino acid sequence selected from ASYNYDA (SEQ ID NO:01), AQLSTLA (SEQ ID NO:02), QLMSADS (SEQ ID NO:03), LPLHSLS (SEQ ID NO:04), and TGPTIQH (SEQ ID NO:05), and wherein the polypeptide is capable of binding to a tumor cell, wherein the administering provides for delivery of the therapeutic agent to the cancer cell in the subject. In some embodiments, the composition further includes at least one of a pharmaceutically acceptable carrier, a pharmaceutically acceptable diluent, a pharmaceutically acceptable excipient and a pharmaceutically acceptable adjuvant. In some embodiments, the therapeutic agent is a cytotoxic agent, a cytostatic agent, an immunomodulating agent, or a radiation emitting agent. In certain embodiments, the therapeutic agent is a chemotherapeutic agent. In some embodiments, the tumor cell is an adenocarcinoma cell, such as an esophageal cancel cell.

Another feature of the present invention is a kit for detecting presence or absence of a tumor cell in a subject, including a composition comprising a polypeptide coupled to a detectable molecule to a subject, wherein the polypeptide comprises up to 50 amino acids in length and an amino acid sequence selected from ASYNYDA (SEQ ID NO:01), AQLSTLA (SEQ ID NO:02), QLMSADS (SEQ ID NO:03), LPLHSLS (SEQ ID NO:04), and TGPTIQH (SEQ ID NO:05), and wherein the polypeptide is capable of binding to a tumor cell. In certain embodiments, the detectable molecule comprises a chelator, a complexed metal, an enriched isotope, radioactive material, a paramagnetic substance, an affinity label, a fluorescent label, a luminescent label, a PET-active substance or a SPECT-active substance. In some embodiments, the detectable molecule is fluorescein or a fluorescein derivative. In some embodiments, the detectable molecule is rhodamine or a rhodamine derivative. In some embodiments, the tumor cell is an adenocarcinoma cell, such as an esophageal cancel cell.

These and other objects, advantages, and features of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

The patent or application file contains at least one drawing executed in color. Copies of this patent or application publication with color drawing(s) will be provided by the U.S. Patent and Trademark Office upon request and payment of the necessary fee.

Included in the drawings are the following figures:

Figure 1:
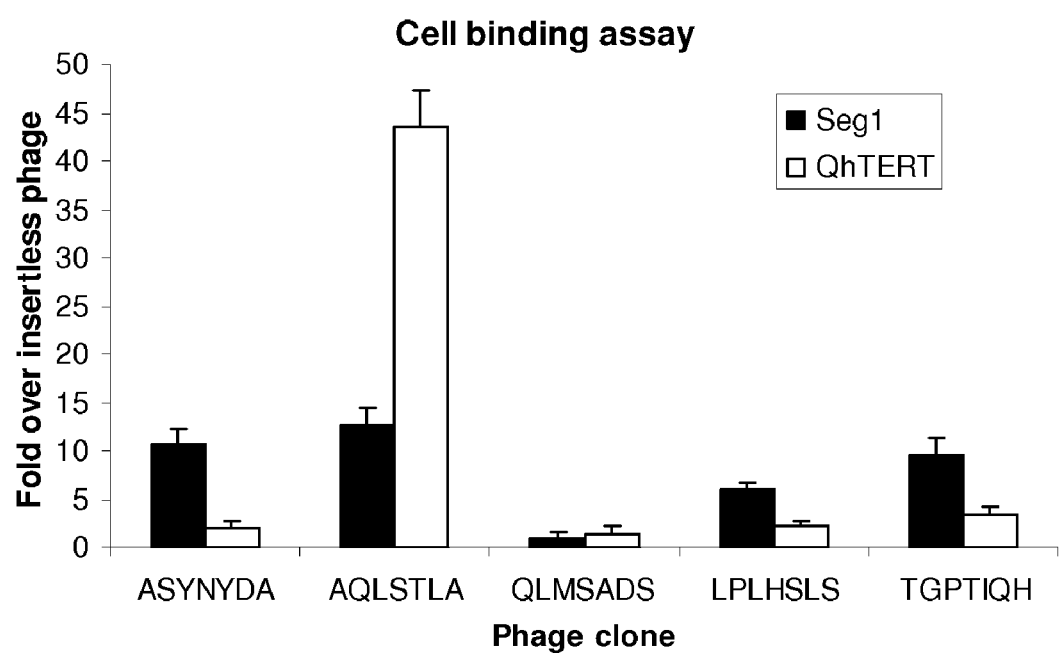

FIG. 1 shows results of a cell binding assay of phage clones relative to insertless phage control. Individual phage clones ($2 \times 10^{11}$ pfu) were incubated at room temperature for 30 min with Seg1 and Q-hTERT cells. The columns represent the mean of measurements from three wells and the bars represent the standard deviation (SD). P-values for each group were calculated using student's t test. Phage clone "17" displaying peptide "ASYNDA" was shown to have a 5-times higher binding to Seg1 cells than Q-hTERT cells relative to insertless phage. *P=0.004

Figure 2:
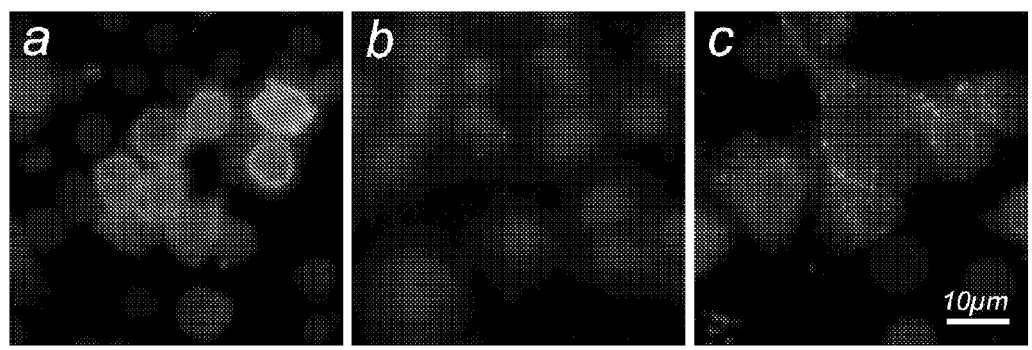

FIG. 2 shows phage binding to Seg1 cells (esophageal adenocarcinoma), (cells were incubated with $1 \times 10^{11}$ pfu phage displaying peptide-ASYNYDA in PBS/1%BSA for 30 min. Presence of phage was detected with polyclonal rabbit anti-M13 antibody and FITC-conjugated mouse anti-rabbit secondary antibody. Panel a shows that phage-ASYNYDA binds to the plasma membrane of Seg1 cells with limited binding to the cytoplasm. Panel c shows that phage-ASYNYDA does not bind to QhTERT cells (Barrett's, non-dysplasia). Slides were mounted in Vectashield mounting medium containing DAPI. Panel B shows that insertless phage control did not bind on Seg-1 cells.

Figure 3:
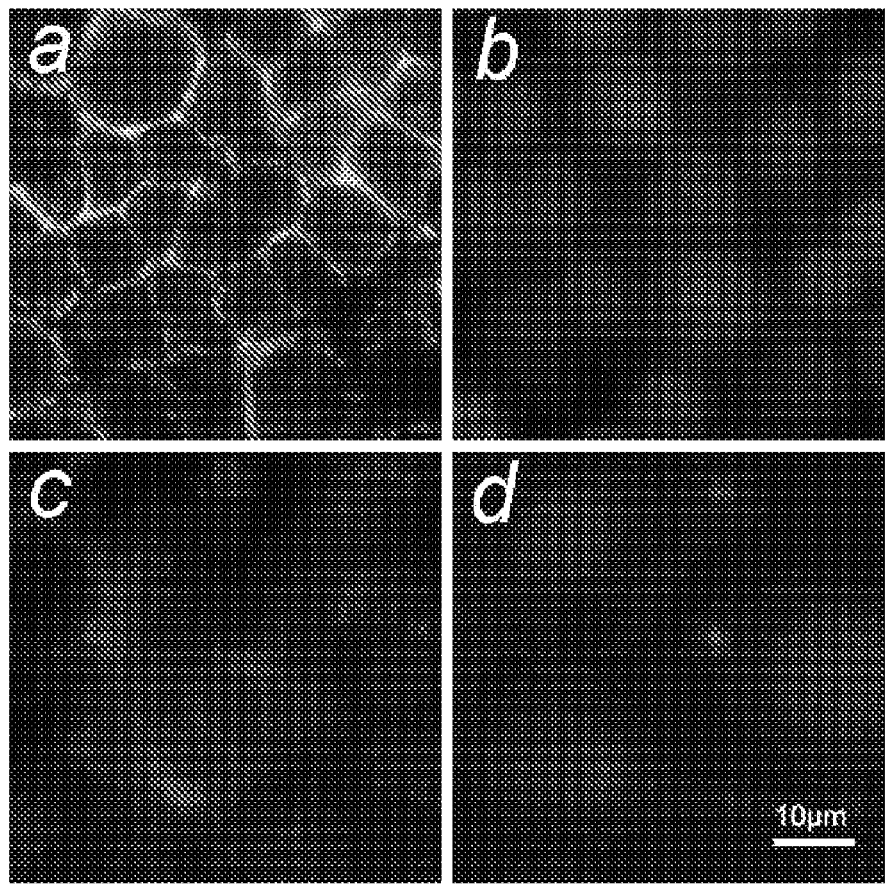

FIG. 3 shows peptide binding to different cell lines. FITC-conjugated peptide (100 µmol) was incubated with Seg1 (Panel a), OE21 (Panel c), QhTERT (Panel d) cells. Peptide binding were found in plasma membrane of >90% of Seg1 cells (Panel a). Peptide ASYNYDA didn't binding on OE21 (Panel c), QhTERT (Panel d) cells. Scrambled FITC-conjugated peptide exhibited no binding to Seg1 cells (Panel b) or other cells.

Figure 4:
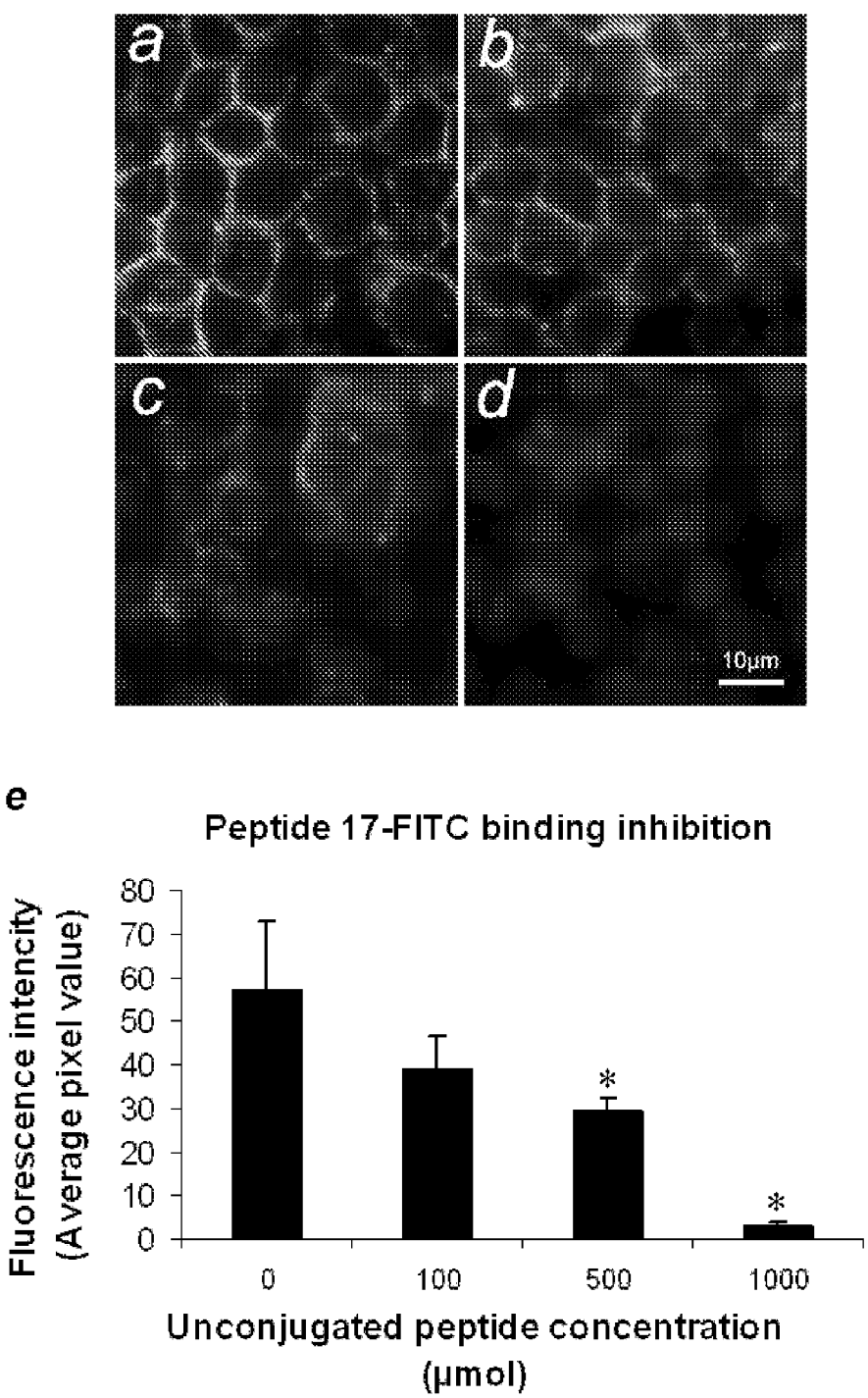

FIG. 4 shows inhibition of peptide binding. Binding of (Panel a) FITC-conjugated peptide can be inhibited by (Panel b) 100 µmol, (Panel c) 500 µmol, and (Panel d) 1000 µmol of unconjugated peptide. Unconjugated peptide was incubated with Seg1 cells 15 min prior to adding of FITC-conjugated peptide in three different concentrations. Panel e shows average fluorescence pixel intensity calculated using three 400× power images. Error bars represent mean±s.e.m. for 3 images. *P<0.01.

Figure 5:
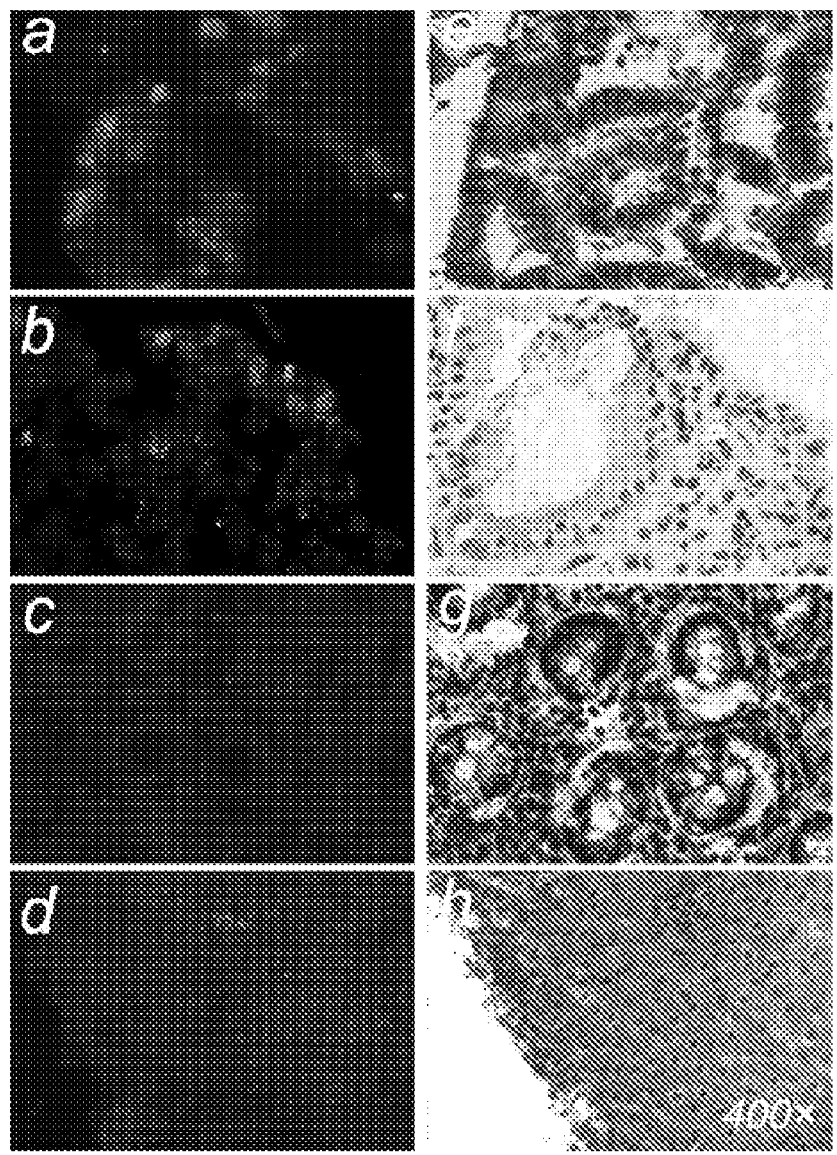

FIG. 5 shows peptide binding on human tissue. Peptide ASYNYDA bound to Barrett's with high-grade dysplasia (HGD) (Panel a), Barrett's (Panel b), but did not bind duodenal mucosa (Panel c) or adjacent normal esophageal mucosa (Panel d). Specimens were incubated with 100 µmol FITC-conjugated peptide in PBS (Panels a, b, c, d). Hematoxylin and eosin staining (Panels e, f, g, h) was performed on adjacent sections to show the pathology diagnosis. In HGD tissue the binding site is a group of consecutive cells located in the lining of esophageal. In normal Barrett's mucosa the binding site is sporadic separated cells in some area of mucosa.

Figure 6:
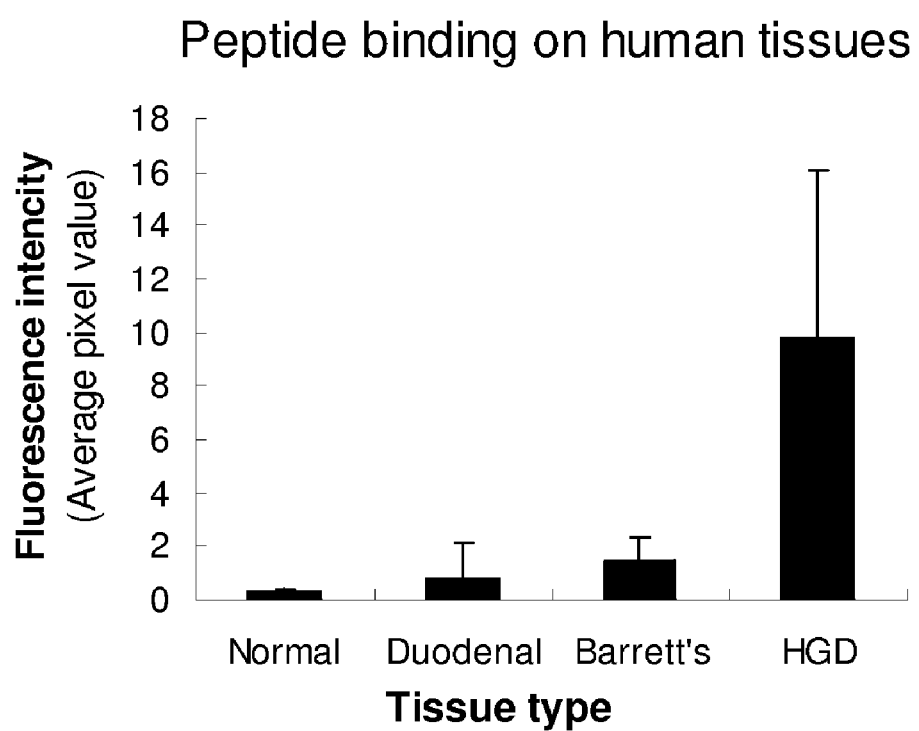

FIG. 6 is a graph showing quantization of peptide binding of FIG. 5 analyzed by NIH image J software, which shows peptide ASYNYDA has higher preferential bind on HGD than other tissues. P<0.01

Figure 7:
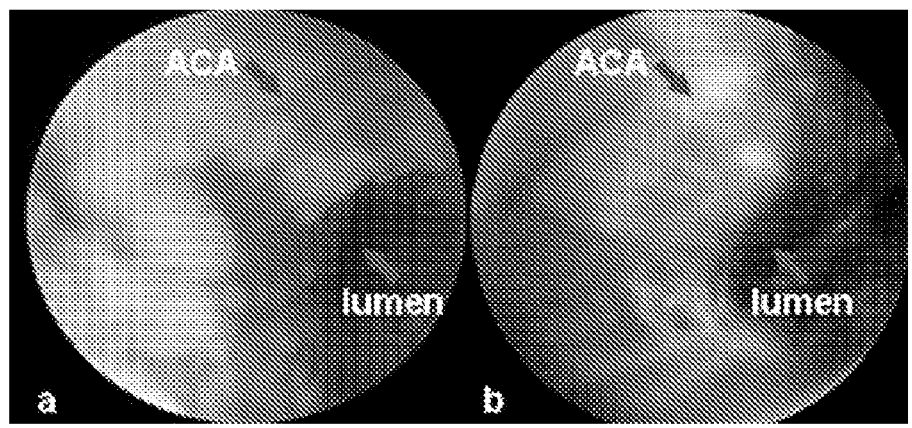

FIG. 7 shows in vivo macroscopic images of rat adenocarcinoma. Panel a shows a white light endoscopic image of the distal esophagus of a rat with an esophago-jejunal (EGJ) anastamosis reveals the presence of an esophageal adenocarcinoma (ACA) present within a patch of Barrett's esophagus. Panel b shows a fluorescence image collected after target peptide was topically administered. Unbound peptide was rinsed off after 5 minutes of incubation, and reveals increased fluorescence intensity at the site of the lesion.

Figure 8:
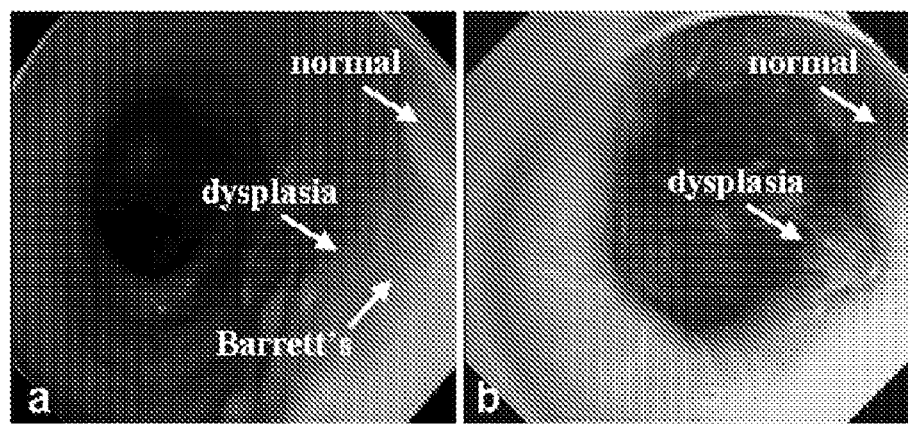

FIG. 8 shows macroscopic imaging of high-grade dysplasia in Barrett's metaplaisa. Endoscopic images collected in vivo of distal esophagus in human subject with Barrett's esophagus and high grade dysplasia on white-light endoscopy (Panel a) and fluorescence imaging (Panel b). Topically administered FITC-labeled target peptide reveals increased fluorescence intensity at the site of the lesion confirmed to be high-grade dysplasia on histopathology.

Figure 9:
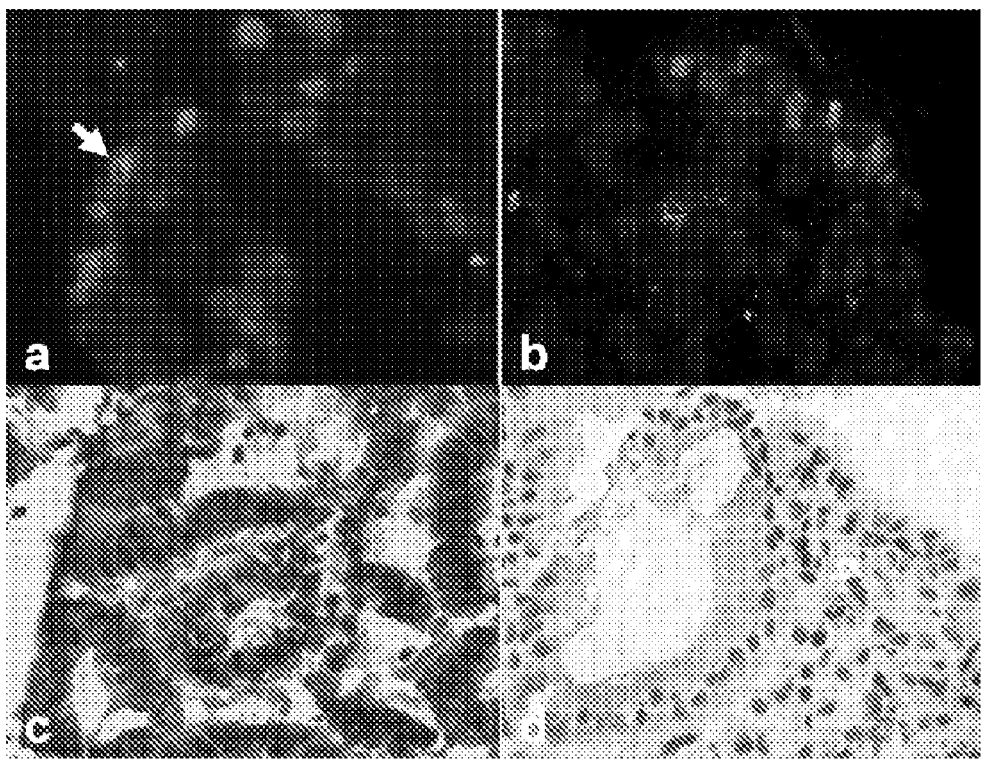

FIG. 9 shows binding of target peptide to esophagus. Significant binding is seen to Barrett's mucosa with high-grade dysplasia (Panel a), and minimal binding is seen to Barrett's tissue with no dysplasia on frozen section (Panel b). Routine histology (H&E) of corresponding images is shown in Panel c and Panel d, magnification 400×.

DEFINITIONS

Unless defined otherwise, all technical and scientific terms used herein have the same meaning as commonly understood by those of ordinary skill in the art to which this invention pertains. Any methods and materials similar or equivalent to those described herein can be used in the practice or testing of the present invention, the described methods and materials being exemplary.

The terms "tumor cell" or "cancer cell", used either in the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells.

An "individual", "subject", or "patient" is a vertebrate, preferably a mammal, more preferably a human. Non-human mammals include, but are not limited to, farm animals, sport animals, and pets.

As used herein, "treatment" refers to clinical intervention in an attempt to alter the natural course of the individual, or cell being treated, and may be performed either for prophylaxis or during the course of clinical pathology. Desirable effects include preventing occurrence or recurrence of disease, alleviation of symptoms, diminishment of any direct or indirect pathological consequences of the disease, preventing metastasis, lowering the rate of disease progression, amelioration or palliation of the disease state, and remission or improved prognosis.

The "pathology" associated with a disease condition is anything that compromises the well-being, normal physiology, or quality of life of the affected individual. This may involve (but is not limited to) destructive invasion of affected tissues into previously unaffected areas, growth at the expense of normal tissue function, irregular or suppressed biological activity, aggravation or suppression of an inflammatory or immunological response, increased susceptibility to other pathogenic organisms or agents, and undesirable clinical symptoms such as pain, fever, nausea, fatigue, mood alterations, and such other features as may be determined by an attending physician.

An "effective amount" is an amount sufficient to effect a beneficial or desired clinical result, particularly the generation of an immune response, or noticeable improvement in clinical condition. An immunogenic amount is an amount sufficient in the subject group being treated (either diseased or not) to elicit an immunological response, which may comprise either a humoral response, a cellular response, or both. In terms of clinical response for subjects bearing a neoplastic disease, an effective amount is amount sufficient to palliate, ameliorate, stabilize, reverse or slow progression of the disease, or otherwise reduce pathological consequences of the disease. An effective amount may be given in single or divided doses. Exemplary quantities for use in an effective amount are given elsewhere in this disclosure.

The terms "polypeptide" and "protein", interchangeably used herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The term "polynucleotide" refers to polymeric forms of nucleotides of any length, either ribonucleotides or deoxynucleotides. Thus, these terms include, but are not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. These terms further include, but are not limited to, mRNA or cDNA that comprise intronic sequences (see, e.g., Niwa et al. (1999) Cell 99(7):691-702). The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidites and thus can be an oligodeoxynucleoside phosphoramidate or a mixed phosphoramidate-phosphodiester oligomer. Peyrottes et al. (1996) Nucl. Acids Res. 24:1841-1848; Chaturvedi et al. (1996) Nucl. Acids Res. 24:2318-2323. A polynucleotide may comprise modified nucleotides, such as methylated nucleotides and nucleotide analogs, uracyl, other sugars, and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support. The term "polynucleotide" also encompasses peptidic nucleic acids (Pooga et al Curr Cancer Drug Targets. (2001) 1:231-9).

A composition (e.g. a polynucleotide, polypeptide, antibody, or host cell) that is "isolated" or "in substantially isolated form" refers to a composition that is in an environment different from that in which the composition naturally occurs. For example, a polynucleotide that is in substantially isolated form is outside of the host cell in which the polynucleotide naturally occurs, and could be a purified fragment of DNA, could be part of a heterologous vector, or could be contained within a host cell that is not a host cell from which the polynucleotide naturally occurs. The term "isolated" does not refer to a genomic or cDNA library, whole cell total protein or mRNA preparation, genomic DNA preparation, or an isolated human chromosome. A composition which is in substantially isolated form is usually substantially purified.

As used herein, the term "substantially purified" refers to a compound (e.g., a polynucleotide, a polypeptide or an antibody, etc.,) that is removed from its natural environment and is usually at least 60% free, preferably 75% free, and most preferably 90% free from other components with which it is naturally associated. Thus, for example, a composition containing A is "substantially free of" B when at least 85% by weight of the total A+B in the composition is A. Preferably, A comprises at least about 90% by weight of the total of A+B in the composition, more preferably at least about 95% or even 99% by weight. In the case of polynucleotides, "A" and "B" may be two different genes positioned on different chromosomes or adjacently on the same chromosome, or two isolated cDNA species, for example.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACS). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 by upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The term "assessing" includes any form of measurement, and includes determining if an element is present or not. The terms "determining", "measuring", "evaluating", "assessing" and "assaying" are used interchangeably and include quantitative and qualitative determinations. Assessing may be relative or absolute. "Assessing the presence of" includes determining the amount of something present, and/or determining whether it is present or absent. As used herein, the terms "determining," "measuring," and "assessing," and "assaying" are used interchangeably and include both quantitative and qualitative determinations.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The practice of the present invention will employ, unless otherwise indicated, conventional techniques of molecular biology, microbiology, cell biology, biochemistry and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal-Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); and "PCR: The Polymerase Chain Reaction", (Mullis et al., eds., 1994).

General procedures for the preparation and administration of pharmaceutical compositions are outlined in Remington's Pharmaceutical Sciences 18th Edition (1990), E. W. Martin ed., Mack Publishing Co., Pa.

All patents, patent applications, articles and publications mentioned herein, both supra and infra, are hereby incorporated herein by reference in their entirety.

DETAILED DESCRIPTION OF THE INVENTION

Before the present invention described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the compound" includes reference to one or more compounds and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Introduction

The present invention is based on the finding that a group of peptides having specific amino acid sequences are capable of selectively targeting tumors, especially primary tumors and metastases, in vivo and tumor cells in vitro. Thus, the peptides of this invention, when administered to a human or animal subject, are capable of selectively binding to tumors but do not bind to normal tissue in the body.

The tumor targeting peptides according to the present invention were identified by bio-panning of phage display libraries. Phage display is a method whereby libraries of random peptides are expressed on the surface of a bacteriophage as part of the phage capsid protein pill by insertion of its encoding DNA sequence into gene III of the phage genome. In general, the libraries display 3-5 copies of each individual peptide per phage particle (Smith and Scott, 1993, Methods Enzymol., 217: 228-257).

As further described below, the tumor targeting peptides of the present invention as useful in cancer therapy as well as diagnostics. For example, the targeting peptide may be covalently or non-covalently linked to a therapeutic agent, such as a chemotherapeutic agent, and administered to a patient to provide for targeted delivery of the therapeutic agent, thereby reducing the toxicity of the therapeutic agent to non-cancer tissues. In addition, the tumor targeting peptides may be conjugated to a detectable molecule and used to identify the presence or absence of a cancer cell, such as adenocarcinoma, in a subject Likewise, the tumor targeting peptides and detectable molecule complex may be used to monitor the success of a cancer treatment regimen in a subject. For example, the complex may be used to monitor the size, spread, extent of growth, or reduction in size of the tumor in response to treatment.

The present invention is described in further detail below.

Compositions

As noted above the present invention provides tumor targeting peptides having specific amino acid sequences that are capable of selectively targeting tumors, especially primary tumors and metastases, in vivo and tumor cells in vitro. The tumor targeting peptides can range from about 2 amino acids in length to about 50 amino acids, including polypeptides ranging from about 2 to about 40, with from about 2 to about 30 being of particular interest, such as from about 2 to about 20 amino acids in length. Generally, tumor targeting peptides may be about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length. In certain embodiments, the tumor targeting peptides will not exceed 20 amino acids in length. Exemplary tumor targeting peptides, include ASYNYDA (SEQ ID NO:01); AQLSTLA (SEQ ID NO:02); QLMSADS (SEQ ID NO:03); LPLHSLS (SEQ ID NO:04); and TGPTIQH (SEQ ID NO:05).

Generally, the terms "targeting" or "binding" stand for adhesion, attachment, affinity or binding of the targeting units of this invention to tumors, tumor cells and/or tumor tissue to the extent that the binding can be objectively measured and determined e.g., by peptide competition experiments in vivo or ex vivo, on tumor biopsies in vitro or by immunological stainings in situ, by fluorescence determination of tumors in vivo, or by other methods known by those skilled in the art. Tumor targeting means that the targeting peptides specifically bind to tumors when administered to a human or animal body. Another term used in the art for this specific association is "homing". Targeting peptides according to the present invention are considered to be "bound" to the tumor target in vitro, when the binding is strong enough to withstand normal sample treatment, such as washes and rinses with physiological saline or other physiologically acceptable salt or buffer solutions at physiological pH, or when bound to a tumor target in vivo long enough for the effector moiety to exhibit its function on the target.

The binding of the present targeting peptides to tumors is "selective" meaning that they do not bind to normal cells and organs, or bind to such to a significantly lower degree as compared to tumors.

According to the present invention, the amino acids of the tumor targeting peptides may be as provided above, or a structural or functional analogue thereof characterized either by its ability to structurally mimic the above noted amino acids, such as tyrosine, for example by virtue of comprising a ring structure of a similar or related type, as compared to the ring structure of tyrosine; or by virtue of comprising another structure that sterically or electrically can be considered as an equivalent of the ring structure of tyrosine. Typically, structural and functional analogues of tyrosine may also be characterized by their ability to mimic the acid-base or electric or bond-conjugation or hydrogen-bond-formation or aromatic or other functional or related properties of tyrosine, e.g. by comprising one or more aromatic rings, one or more hydroxyl groups, often preferably phenolic hydroxyl groups, etc., as is understood by those skilled in the art. For example, many types of structural and functional analogues of alanine, serine, asparagine, aspartic acid, and tyrosine are commercially available, and many more are described in the chemical literature known by those skilled in the art, and further ones can be synthesized by those skilled in the art.

The tumor targeting peptides according to the present invention may optionally comprise unit(s) such as linkers, solubility modifiers, stabilizers, charge modifiers, spacers, lysis or reaction or reactivity modifiers, internalizing units or internalization enhancers or membrane interaction units or other local route, attachment, binding or distribution affecting units or other related units at either the C-terminus or the N-Terminus Such additional units of the tumor targeting peptides according to the present invention may be coupled to each other by any means suitable for that purpose.

The terms "C-terminus" and "C-terminal" refer to the carboxylic end of the peptide chain, which may be free, or coupled to another moiety. Moreover, the terms "N-terminus" and "N-terminal" refer to the amino end of the peptide chain, which may be free, or coupled to another moiety.

As noted above, the tumor targeting peptides may be linked to an effector molecule that provides for a therapeutic (biological, chemical or physical) effect on the targeted tumor; properties that enable the detection or imaging of tumors or tumor cells for diagnostic purposes; as well as binding abilities that relate to the use of the targeting peptides in different applications.

It is also contemplated that the compositions may include one or more targeting peptide, such as 2, 3, 4, 5, or more of the same or different targeting peptides in complex with one or more effector molecules, such as 2, 3, 4, 5, or more of the same or different effector molecules. The plurality of targeting peptides may be linked in tandem N-terminus to C-terminus, or vice versa, format, or the plurality of targeting peptides may be linked separately to the effector molecule at their N-terminus or C-terminus ends.

The effector molecule, such as a detectable moiety or therapeutic moiety, may be linked to the targeting units by any type of bond or structure or any combinations of them that are strong enough so that most, or preferably all or essentially all of the effector molecule of the targeting peptide remain linked to the targeting peptide during the essential (necessary) targeting process, e.g. in a human or animal subject or in a biological sample under study or treatment.

The effector molecule or parts of them may remain linked to the targeting peptide, or they may be partly or completely hydrolyzed or otherwise disintegrated from the latter, either by a spontaneous chemical reaction or equilibrium or by a spontaneous enzymatic process or other biological process, or as a result of an intentional operation or procedure such as the administration of hydrolytic enzymes or other chemical substances. It is also possible that the enzymatic process or other reaction is caused or enhanced by the administration of a targeted substance such as an enzyme in accordance with the present invention.

One possibility is that the effector molecule or parts thereof are hydrolyzed from the targeting peptide or hydrolyzed into smaller units by the effect of one or more of the various hydrolytic enzymes present in tumors (e.g., intracellularly, in the cell membrane or in the extracellular matrix) or in their near vicinity.

Taking into account that the targeting according to the present invention may be very rapid, even non-specific hydrolysis that occurs every-where in the body may be acceptable and usable for hydrolyzing one or more effector molecule(s) intentionally, since such hydrolysis may in suitable cases (e.g., steric hindrance, or even without any such hindering effects) be so slow that the targeting agents are safely targeted in spite of the presence of hydrolytic enzymes of the body, as those skilled in the art very well understand.

The formation of insoluble products or products rapidly absorbed into cells or bound to their surfaces after hydrolysis may also be beneficial for the targeted effector molecule or their fragments etc. to remain in the tumors or their closest vicinity.

In some embodiments, the targeting peptide may be complexed with the effector molecule via a linker A large number of suitable linker units are known in the art. Examples of suitable linkers, include, but are not limited to linking units that comprise amino groups: cyclic anhydrides, dicarboxylic or multivalent, optionally activated or derivatized, carboxylic acids, compounds with two or more reactive halogens or compounds with at least one reactive halogen atom and at least one carboxyl group; linking units that comprise carboxyl groups or derivatives thereof: compounds with at least two similar or different groups such as amino, substituted amino, hydroxyl, —NHNH$_2$ or substituted forms thereof, other known groups for the purpose (activators may be used); linking an amino group and a carboxyl group: for example amino acids or their activated or protected forms or derivatives; linking a formyl group or a keto group to another group: a compound comprising e.g. at least one —N—NH$_2$ or —O—NH$_2$ or =N—NH$_2$ group or their like; linking several amino-comprising units: polycarboxylic substances such as EDTA, DTPA or polycarboxylic acids, or anhydrides, esters or acyl halides thereof; linking a substance comprising an amino group to a substance comprising either a formyl group or a carboxyl group: hydrazinocarboxylic acids or their like, preferably so that the hydrazino moiety or the carboxyl group is protected or activated, such as 4-(FMOC-hydrazino)benzoic acid; linking an organic structure to a metal ion: substances that can be coupled to the organic structure (e.g. by virtue of their COOH groups or their NH$_2$ groups) or that are integral parts of it, and that in addition comprise a polycarboxylic part, for example an EDTA- or DTPA-like structure, peptides comprising several histidines or their like, peptides comprising several cysteines or other moieties comprising an —SH group each, or other chelating agents that comprise functional groups that can be used to link them to the organic structure.

A large variety of the above substances and of other types of suitable linking agents is known in the art.

Detection Moiety

In some embodiments the effector molecule is a detectable molecule that is capable of providing direct or indirect detection of a cancer cell in vitro and in vivo when complexed to a targeting peptide. Examples of molecules suitable for direct or indirect detection include presence of an immunogenic structure, or the presence of an antibody or antibody fragment or antibody-type structure, or the presence of a gold particle, or the presence of biotin or avidin or other protein, and/or luminescent and/or fluorescent and/or phosphorescent activity or the ability to enhance detection of tumors, tumor cells, endothelial cells and metastases in electron microscopy, light microscopy (UV and/or visible light), infrared microscopy, atomic force microscopy or tunneling microscopy, and so on.

Exemplary detectable molecules according to the present invention may comprise a chelator; a complexed metal such as a rare earth metal, a paramagnetic metal, a fluorescent metal (e.g. Eu, Tb or Ho), a radioactive metal, a PET-active substance or a SPECT-active substance; an enriched isotope; radioactive material such as beta-emittor or alpha emittor; a paramagnetic substance; an affinity label; a fluorescent label (e.g. fluorescein or rhodamine) or a luminescent label. Exemplary detectable labels suitable for use include fluorescein or rhodamine, as well as fluorescein or rhodamine derivatives, such as fluorescein isothiocyanate (FITC), Oregon Green, Tokyo Green, SNAFL, carboxynaphthofluorescein, Alexa 488, DyLight 488, tetramethylrhodamine (TAMRA) and its isothiocyanate derivative (TRITC), sulforhodamine 101, Rhodamine Red, Alexa 546, Alexa 555, Alexa 633, DyLight 549 and DyLight 633 etc.

Methods of measuring and/or monitoring fluorescence are well known in the art. Both qualitative assessments (positive/negative) and quantitative assessments (comparative degree of fluorescence) may be provided by the present methods. Brightness can be measured using any known method, including, but not limited to, visual screening, spectrophotometry, spectrofluorometry, fluorescent microscopy, etc.

Therapeutic Moiety

A variety of different types of molecules may be used as a therapeutic agent in complex with a targeting peptide in a given method. As such, therapeutic agents of interest include, but are not limited to: small or low molecular weight compounds, peptides, polypeptides and proteins (including intrabodies); nucleic acids, e.g., antisense molecules, and the like. Of interest in certain embodiments are small molecule compounds. Naturally occurring or synthetic small molecule compounds of interest include numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, nucleic acids, fatty acids, steroids, purines, pyrimidines, derivatives, structural analogs or combinations thereof.

Other exemplary molecules suitable for use as therapeutic agents in complex with a targeting peptide in a given method include conventional chemotherapeutic agents, such as cytotoxic agents, antineoplastic agents, and the like. Cytotoxic agents that act to reduce cellular proliferation are known in the art and widely used. Such agents include alkylating agents, such as nitrogen mustards, e.g. mechlorethamine, cyclophosphamide, melphalan (L-sarcolysin), etc.; and nitrosoureas, e.g. carmustine (BCNU), lomustine (CCNU), semustine (methyl-CCNU), streptozocin, chlorozotocin, etc. Antimetabolite agents include pyrimidines, e.g. cytarabine (CYTOSAR-U), cytosine arabinoside, fluorouracil (5-FU), floxuridine (FUdR), etc.; purines, e.g. thioguanine (6-thioguanine), mercaptopurine (6-MP), pentostatin, fluorouracil (5-FU) etc.; and folic acid analogs, e.g. methotrexate, 10-propargyl-5,8-dideazafolate (PDDF, CB3717), 5,8-dideazatetrahydrofolic acid (DDATHF), leucovorin, etc. Other natural products include azathioprine; brequinar; alkaloids and synthetic or semi-synthetic derivatives thereof, e.g. vincristine, vinblastine, vinorelbine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithromycin); anthracenediones, e.g. mitoxantrone; azirinopyrrolo indolediones, e.g. mitomycin; and the like. Other chemotherapeutic agents include metal complexes, e.g. cisplatin (cis-DDP), carboplatin, etc.; ureas, e.g. hydroxyurea; and hydrazines, e.g. N-methylhydrazine. Other anti-proliferative agents of interest include immunosuppressants, e.g. mycophenolic acid, thalidomide, desoxyspergualin, azasporine, leflunomide, mizoribine, azaspirane (SKF 105685), etc. The antineoplastic agents taxols (or taxanes) hyperstabilize polymerized microtubules, leading to mitotic arrest and cytotoxicity in proliferating cells. Taxanes (or taxols), such as paclitaxel, docetaxel, etc. are of interest. Also of interest are the microtubule stabilizing epothilones (see Bollag et al. (1995) Cancer Research, Vol 55, Issue 11 2325-2333, herein incorporated by reference with respect to teachings of the class, and use thereof of these chemotherapeutic agents), e.g. epothilone A and epothilone B. Retinoids, e.g. vitamin A, 13-cis-retinoic acid, trans-retinoic acid, isotretinoin, etc.; carotenoids, e.g. beta-carotene, vitamin D, etc. Retinoids regulate epithelial cell differentiation and proliferation, and are used in both treatment and prophylaxis of epithelial hyperproliferative disorders.

Synthesis of Targeting Peptides

The targeting peptides can be prepared using a variety of methods well known in the art, including, but not limited to recombinant methods as well as synthetic methods. In some embodiments, the targeting peptides according to the present invention are synthesized by synthetic methods. Peptides can be synthesized by a large variety of well-known techniques, such as solid-phase methods (FMOC-, BOC-, and other protection schemes, various resin types), solution methods (FMOC, BOC and other variants) and combinations of these. Automated apparatuses/devices for the purpose are available commercially, as are also routine synthesis and purification services. All of these approaches are very well known to those skilled in the art.

In certain embodiments, one or more protecting groups are used during synthesis, a large variety of which are known in the art, such as FMOC, BOC, and trityl groups and other protecting groups. Protecting groups are often used for protecting amino, carboxyl, hydroxyl, guanyl and --SH groups, and for any reactive groups/functions.

Protection may also be orthogonal and/or semi/quasi/pseudo-orthogonal. Protecting and activating groups, substances and their uses are exemplified in the Examples and are described in the references cited herein, and are also described in a large number of books and other sources of information commonly known in the art.

The targeting units and agents according to the present invention may also be prepared as fusion proteins or by other suitable recombinant DNA methods known in the art. Such an approach for preparing the peptides according to the present invention is preferred especially when the effector units and/or other optional units are peptides or proteins. One example of a useful protein effector unit is glutathione-S-transferase (GST).

Therapeutic Methods

As summarized above and described in more detail below, the subject invention provides therapeutic methods. In a broad sense, such methods in certain embodiments may be viewed as methods of targeted delivery of a therapeutic agent, such as chemotherapy agent, complexed either covalently or non-covalently with a targeting peptide to a cancer cell, such as adenocarcinoma, in a subject. Exemplary conditions include benign Esophageal Lesions, Barretts Esophagus and other Esophageal Hyperplasia and Dysplasia, and Esophageal Cancer, including Squamous Cell Carcinoma, Adenocarcinoma, Carsinosarcoma, Pseudosarcoma, and Sarcoma.

By "effective amount" is meant a dosage sufficient to produce the desired result, e.g., an inhibition of cellular movement, or an improvement in a disease condition or the symptoms associated therewith associated with or resulting from unwanted cellular movement. The agent may be administered to the host using any convenient means capable of producing the desired result. Thus, the agent can be incorporated into a variety of formulations for therapeutic administration. More particularly, the agent can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. As such, administration of the agent can be achieved in various ways, including oral, buccal, rectal, parenteral, intraperitoneal, intradermal, transdermal, intracheal, etc., administration. In pharmaceutical dosage forms, the agent may be administered alone or in combination with other pharmaceutically active compounds. The following methods and excipients are merely exemplary and are in no way limiting.

For oral preparations, the agent can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agent can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agent can be utilized in aerosol formulation to be administered via inhalation. The agent can be formulated into pressurized acceptable propellants such as dichlorodifluoromethane, propane, nitrogen and the like.

Furthermore, the agent can be made into suppositories by mixing with a variety of bases such as emulsifying bases or water-soluble bases. The agents can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing active agent. Similarly, unit dosage forms for injection or intravenous administration may comprise the active agent in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

The subject methods of these embodiments find use in a variety of different applications, including the treatment of a variety of different disease conditions associated with the presence of cancer cells, e.g., neoplastic disease conditions. As such, one disease condition of particular interest is neoplastic diseases, particularly those characterized by the presence of adenocarcinoma, such as neoplasia in Barrett's Esophagus. By treatment is meant at least an amelioration of the symptoms associated with the disease condition afflicting the host, where amelioration is used in a broad sense to refer to at least a reduction in the magnitude of a parameter, e.g. symptom, associated with the pathological condition being treated, such as size of tumor, rate of growth of tumor, spread of tumor, etc. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Accordingly, the methods of these embodiments of the present invention may be applied to the treatment of a variety of cancers, e.g., of epithelial cell origin. Among these are metastatic cancers of esophagus, including Barrett's esophagus, breast, lung, colon, bladder, lung, gastrointestinal track, endometrium, tracheal-bronchial tractm, pancreas, liver, uterus, nasopharynges and the skin. In certain embodiments, the methods are employed in the treatment of adenocarcinoma of the esophagus, including Barrett's esophagus.

The subject methods may be used in conjunction with other treatment modalities. Other common treatment modalities are discussed below specifically by reference to adenocarcinoma of the esophagus, including Barrett's esophagus. It will be appreciated that similar consideration will apply to treatment of other cancers. The present invention may be used in conjunction with any current or future therapy. Specific representative additional therapies of interest include surgery, radiation, hormonal therapy, chemotherapy, immunotherapy, cryotherapy, etc.

In addition, other therapies of interest include treatment of conditions or symptoms of conditions associated with esophageal cancer. For example, esophageal cancer can often be associated with Barrett's esophagus in which the esophagus, the muscular tube that carries food and saliva from the mouth to the stomach, changes so that some of its lining is replaced by a type of tissue similar to that normally found in the intestine. This process is referred to as intestinal metaplasia. Furthermore, Barrett's esophagus is often associated with the very common condition gastroesophageal reflux disease or GERD. Exemplary compounds that may be administered in combination with the targeting peptide and therapeutic agent complex include antacids, antisecretory drugs, proton pump inhibitors, and the like. Common antacids include, but are not limited to, Alka-Seltzer, Maalox, Mylanta, Pepto-Bismol, Riopan, Rolaids, and the like. Other drugs used to relieve GERD symptoms are antisecretory drugs such as histamine2 ($H_2$) blockers or proton pump inhibitors. Common H2 blockers include, but are not limited to, cimetidine (Tagamet HB), famotidine (Pepcid AC), nizatidine (Axid AR), ranitidine (Zantac 75), and the like. Common proton pump inhibitors include, but are not limited to, esomeprazole (Nexium), lansoprazole (Prevacid), omeprazole (Prilosec), pantoprazole (Protonix), rabeprazole (Aciphex), and the like.

In these embodiments, the agent that modulates the activity of at least one target protein associated with cellular locomotion is administered in combination with the chromatin function inhibiting agent (e.g., paclitaxel or analog thereof). By "in combination with" is meant that an amount of the first locomotion modulatory agent is administered together with an amount of the second chromatin function inhibiting agent. In certain embodiments, the first and second agents are administered sequentially, e.g., where the first agent is administered before or after the second agent. In yet other embodiments, the first and second agents are administered simultaneously, e.g., where the first and second agents are administered at the same time as two separate formulations or are combined into a single composition that is administered to the subject. Regardless of whether the first and second agents are administered sequentially or simultaneously, as illustrated above, the agents are considered to be administered together or in combination for purposes of the present invention. Routes of administration of the two agents may vary, where representative routes of administration are described in greater detail below.

Methods

As noted above, the present invention also provides methods of detecting the presence or absence of neoplasia in a subject, such as adenocarcinoma, including esophageal cancer, by administering a tumor targeting peptides coupled directly or indirectly to a detectable molecule to a subject, detecting a level of binding of the polypeptide coupled to a detectable molecule in the subject as compared to a negative control, where an increase in binding of the polypeptide coupled to the detectable molecule as compared to a negative control indicates the presence of a tumor cell in the subject As such, the present invention also relates to diagnostic compositions comprising an effective amount of at least one targeting peptide and a detectable molecule, such as fluorescein, according to the present invention. A diagnostically effective amount of the targeting agents according to the present invention may range from 1 femtomol to 10 mmols, depending for example on the effector unit of choice. In addition to the targeting agent, a diagnostic composition according to the present invention may, optionally, comprise carriers, solvents, vehicles, suspending agents, labeling agents and other additives commonly used in diagnostic compositions. Such diagnostic compositions are useful in diagnosing tumors, tumor cells and metastasis, especially tumors of the colon, more specifically colon primary tumors and metastases, in animals as well as in human subjects.

A diagnostic composition according to the present invention may be formulated as a liquid, gel or solid formulation or as an inhalation formulation, etc., preferably as an aqueous liquid, containing a targeting agent according to the present invention in a concentration ranging from about $1 \times 10^{-10}$ mg/1 mg/1 to $25 \times 10^4$ mg/l. The compositions may further comprise stabilizing agents, detergents, such as polysorbates, as well as other additives. The concentrations of these components may vary significantly depending on the formulation used. The diagnostic compositions may be used in vivo or in vitro.

In some embodiments, characterization of disease activity yields information concerning progression of the neoplasia in the human subject, e.g. whether progression of the neoplasia has accelerated or slowed. For example, the initial characterization date, i.e. the level of tumor cells, such as esophageal cancer cells, detected in the human subject, could be employed as a baseline value to evaluate subsequent testings, e.g. at some time following the initial testing, e.g. 3 months. If the level of tumor cells decreases in subsequent testing, this indicates that the neoplasia is not progressing and may be resolving, as a result of, for example, treatment. Alternatively, if the level of tumor cells increases, this indicates that the neoplasia is progressing in severity.

In some embodiments, the subject methods of the present invention may be used in the treatment a human subject for a neoplastic disease, such as esophageal cancer. In such embodiments, the subject methods are employed to first determine whether a human subject suffers from neoplasia (or the severity of the disease) by determining the level of tumor cells present in the human subject according the subject methods. Once, a determination has been made with respect to whether the human subject suffers from neoplasia, a treatment protocol is identified for the human subject. Treatment protocols for cancer are well know in the art and include, but are not limited to, surgery, chemotherapy, radiotherapy, and the like.

In other embodiments, characterization data of the level of cancer cells present in a human subject obtained by the subject methods may also be used to determine whether a particular therapeutic regimen is having positive affects with respect to the progression of the pancreatic disease. For example, at various time periods during the course of treatment, the subject methods may be performed to obtain a reading of the amount of a cancer cell present in a human subject under a particular treatment regimen. If the level of the cancer cell is increasing, this indicates that the treatment regimen is not having the desired effect, where the desired effect is to slow the progression of the cancer. Alternatively, if the level of a cancer cell is decreasing, this indicates that the treatment regimen is working with respect to slowing the progression of the cancer.

Pharmaceutical Compositions

Also provided are pharmaceutical compositions containing the targeting peptide and therapeutic agent complex employed in the subject methods. The targeting peptide and therapeutic agent complex, e.g., in the form of a pharmaceutically acceptable salt, can be formulated for oral or parenteral administration for use in the subject methods, as described above.

By way of illustration, the targeting peptide and therapeutic agent complex, also referred to as the active compound, can be admixed with conventional pharmaceutical carriers and excipients (i.e., vehicles) and used in the form of aqueous solutions, tablets, capsules, elixirs, suspensions, syrups, wafers, and the like. Such pharmaceutical compositions contain, in certain embodiments, from about 0.1 to about 90% by weight of the active compound, and more generally from about 1 to about 30% by weight of the active compound. The pharmaceutical compositions may contain common carriers and excipients, such as corn starch or gelatin, lactose, dextrose, sucrose, microcrystalline cellulose, kaolin, mannitol, dicalcium phosphate, sodium chloride, and alginic acid. Disintegrators commonly used in the formulations of this invention include croscarmellose, microcrystalline cellulose, corn starch, sodium starch glycolate and alginic acid.

A liquid composition will generally consist of a suspension or solution of the compound or pharmaceutically acceptable salt in a suitable liquid carrier(s), for example, ethanol, glycerine, sorbitol, non-aqueous solvent such as polyethylene glycol, oils or water, with a suspending agent, preservative, surfactant, wetting agent, flavoring or coloring agent. Alternatively, a liquid formulation can be prepared from a reconstitutable powder.

For example, a powder containing active compound, suspending agent, sucrose and a sweetener can be reconstituted with water to form a suspension; and a syrup can be prepared from a powder containing active ingredient, sucrose and a sweetener.

A composition in the form of a tablet can be prepared using any suitable pharmaceutical carrier(s) routinely used for preparing solid compositions. Examples of such carriers include magnesium stearate, starch, lactose, sucrose, microcrystalline cellulose and binders, for example, polyvinylpyrrolidone. The tablet can also be provided with a color film coating, or color included as part of the carrier(s). In addition, active compound can be formulated in a controlled release dosage form as a tablet comprising a hydrophilic or hydrophobic matrix.

A composition in the form of a capsule can be prepared using routine encapsulation procedures, for example, by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example, liquid paraffin or fractionated coconut oil can be prepared and filled into a soft gelatin capsule.

Tablet binders that can be included are acacia, methylcellulose, sodium carboxymethylcellulose, poly-vinylpyrrolidone (Povidone), hydroxypropyl methylcellulose, sucrose, starch and ethylcellulose. Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. Additionally, it may be desirable to add a coloring agent to make the dosage form more attractive in appearance or to help identify the product.

The compounds of the invention and their pharmaceutically acceptable salts that are active when given parenterally can be formulated for intramuscular, intrathecal, or intravenous administration.

A typical composition for intramuscular or intrathecal administration will be of a suspension or solution of active ingredient in an oil, for example, arachis oil or sesame oil. A typical composition for intravenous or intrathecal administration will be a sterile isotonic aqueous solution containing, for example, active ingredient and dextrose or sodium chloride, or a mixture of dextrose and sodium chloride. Other examples are lactated Ringer's injection, lactated Ringer's plus dextrose injection, Normosol-M and dextrose, Isolyte E, acylated Ringer's injection, and the like. Optionally, a cosolvent, for example, polyethylene glycol, a chelating agent, for example, ethylenediamine tetraacetic acid, and an antioxidant, for example, sodium metabisulphite may be included in the formulation. Alternatively, the solution can be freeze dried and then reconstituted with a suitable solvent just prior to administration.

The compounds of the invention and their pharmaceutically acceptable salts which are active on rectal administration can be formulated as suppositories. A typical suppository formulation will generally consist of active ingredient with a binding and/or lubricating agent such as a gelatin or cocoa butter or other low melting vegetable or synthetic wax or fat.

The compounds of this invention and their pharmaceutically acceptable salts which are active on topical administration can be formulated as transdermal compositions or transdermal delivery devices ("patches"). Such compositions include, for example, a backing, active compound reservoir, a control membrane, liner and contact adhesive. Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference in its entirety. Such patches may be constructed for continuous, pulsatile, or on demand delivery of pharmaceutical agents.

Optionally, the pharmaceutical composition may contain other pharmaceutically acceptable components, such a buffers, surfactants, antioxidants, viscosity modifying agents, preservatives and the like. Each of these components is well-known in the art. See, for example, U.S. Pat. No. 5,985,310, the disclosure of which is herein incorporated by reference.

Other components suitable for use in the formulations of the present invention can be found in Remington's Pharmaceutical Sciences, Mace Publishing Company, Philadelphia, Pa., 17th ed. (1985).

Kits

The present invention also includes kits and components of kits for diagnosing, detecting, treating, monitoring treatment, or analyzing cancer or cancer cells in vivo and in vitro. Such kits comprise at least one targeting peptide of this invention together with diagnostic entities enabling detection or a therapeutic agent providing for a therapeutic effect in a subject. For example, the kit may comprise for example a targeting peptide coupled to a unit for detection by e g immunological methods, radiation or enzymatic methods or other methods known in the art. Instructions (e.g., written, tape, VCR, CD-ROM, etc.) for carrying out the methods usually will be included in the kit. The kit can also contain, depending on the particular method used (e.g., diagnosing, detecting, treating, monitoring treatment, etc.), other packaged reagents and materials (i.e. wash buffers and the like).

The instructions are generally recorded on a suitable recording medium. For example, the instructions may be printed on a substrate, such as paper or plastic, etc. As such, the instructions may be present in the kits as a package insert, in the labeling of the container of the kit or components thereof (e.g., associated with the packaging or subpackaging), etc. In other embodiments, the instructions are present as an electronic storage data file present on a suitable computer readable storage medium, e.g., CD-ROM, diskette, etc, including the same medium on which the program is presented.

In yet other embodiments, the instructions are not themselves present in the kit, but means for obtaining the instructions from a remote source, e.g. via the Internet, are provided. An example of this embodiment is a kit that includes a web address where the instructions can be viewed from or from where the instructions can be downloaded.

Still further, the kit may be one in which the instructions are obtained are downloaded from a remote source, as in the Internet or world wide web. Some form of access security or identification protocol may be used to limit access to those entitled to use the subject invention. As with the instructions, the means for obtaining the instructions and/or programming is generally recorded on a suitable recording medium.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Methods and Materials

The following methods and materials were used in the below Examples.

Cell lines

An esophageal adenocarcinoma cell line (SEG-1) derived from Barrett's-associated adenocarcinoma of the esophagus was used for the in vitro studies (Soldes et al., Br J Cancer 1999;79:595-603), and squamous esophagus carcinoma cell line OE21 were obtained from ECACC (Rockett et al., Br J Cancer 1997;75:258-63). These cell were maintained in DMEM or RPMI-1640 supplemented with 10% FBS. Barrett's Esophagus cell lines KR-42421 (Q-hTERT), CP-18821 (Go-hTERT, Barrett's with HGD) (Palanca-Wessels et al., Carcinogenesis 2003;24:1183-90), maintained in Keratinocyte-serum free medium supplemented with Bovine Pituitary Extract (BPE) and human recombinant Epidermal Growth Factor (rEGF). All cell lines were incubated at 37° C. in 5% $CO_2$.

Biopanning

The phage library (Ph.D.-7, New England Biolabs, Beverly, Mass.) contains ~$2.8 \times 10^9$ unique sequences, and ~70 copies each was used for the initial biopanning. First, non-specific binding phage were removed from the library by biopanning against ~$5 \times 10^5$ OE21 cells cultured in six well plates. Blocking of non-specific binding was further enhanced by adding 200 μL of 1% BSA diluted in PBS for 30 minutes. Biopanning was performed at room temperature for ~30 minutes with gentle agitation. The supernatant containing unbound phage was collected and added to the next well for another round of clearance. The resulting supernatant was then amplified, precipitated with PEG-NaCl, and then titered.

For the enrichment of phage that binding on esophagus andenocarcinoma, $2 \times 10^{11}$ pfu phage from the former step was added and incubated with Seg-1 cells as above. Unbound phage was discarded. Wash plate 10 times with PBS/0.1%(v/v) Tween-20. The bound phages were eluted with 1 mL of 0.2 M glycine, pH 2.2/0.1% BSA for 8 min. The phage-containing solution was immediately neutralized with 150 μL of 1 M Tris, pH 9.5, then all the eluted phages were applied to second rounds of panning in the same conditions, except that the eluted was changed to two-step. First step elute 2 min discard elute buffer then add elute buffer again incubate for 6 min collect the elute buffer. The third round panning was done following the same protocol.

10 μL of elute buffer containing binding phage from each round were preserved and tittered. 48 Single phage plaques from the last round panning were selected randomly, then amplified in 96 well plate and sequenced (Molecular Cloning Laboratories, Calif., USA). Peptide sequence that shared by more than 2 phage clones was selected as the candidates in the following research. Peptides were analyzed by the National Center of Biotechnology Information BLAST search using the option for short nearly exact matches, to identify human proteins with homologous sequences.

Phage Binding Assay

According to the sequencing results some peptide sequence expressed on more than one phage clones. These phage clones had been amplified respectively for the binding assay. Seg-1 cell and Q-hTERT cell (None dysplasia Barrett's cell line) were growth in 6 well plate. $2 \times 10^{11}$ pfu each single clone phage were incubated with both cell in triple wells. Wild-type (no insert) phage (M13KE, New England Biolabs, Beverly, Mass.) was used as control. The incubation, two-step elution and tittering were done as mentioned above. All the elute phage were tittered to obtain mean values of phage plaque numbers. Fold binding of each phage relative to none insert phage was measured. Different binding of each phage clone on Seg-1 and QhTERT were calculated using student's t test.

Phage Based Immunofluorescence

In order to verify the specific binding of these screened phages, $3 \times 10^4$ Seg-1 and QhTERT cells were seeded in Poly-D-Lysine coated 8-well chamber slides (Fisher scientific) for over night culture to 70%-90% confluence. Blocking and biopanning were performed as above. Cells had been wash 3 times by 200 μL PBS/0.5% TWEEN 20 in room temperature. Rabbit originated Anti-M13 page Antibody (GenWay Biotech, Inc, San Diego, Calif.) were added in 1:100 dilution as primary antibody. Mouse anti-rabbit second antibody (Invitrogen, Carlsbad, Calif.) conjugated with FITC, were then added at 1:1000 for 30 min. Slide were then mounted by Vectashield mounting medium with DAPI (Vector Laboratories, Inc. Burlingame, Calif.).

Peptide Synthesis

The targeted peptide sequence 'ASYNYDA' identified by the phage binding assay was synthesized using standard (F)luorenyl-(m)eth(o)xy-(c)arbonyl (FMOC) chemistry, purified to a minimum of 98% purity using high-performance liquid chromatography (HPLC), and analyzed by reverse phase HPLC and mass spectrometry. The fluorescence dye FITC was conjugated at the C-terminus of the peptide via an flexible 5-amino acid linker (ASYNYDA-GGGSK-FITC). GGGSK is the same linker as this peptide is fused to the coat protein pIII of M13. The targeted peptide was scrambled to form the sequence 'YANSAYD' and synthesized as described above for use as control.

Peptide Binding on Cell Lines $3\times10^4$-$5\times10^4$ Seg-1, OE21, QhTERT cells were grown in chamber slides.

Blocking of non-specific binding to these cells was performed by adding 200 µL of 1% BSA diluted in PBS for 30 min. The cells were then incubated with 100 µmol of the targeted FITC conjugated peptide in serum free media for 15 min in room temperature. The scrambled peptide had been used as control. Wash cells 3-time use 200 µL PBS/0.5% TWEEN 20 in room temperature. Cell were fixed by ice cold Acetone 90 second. Then mounted by Vectashield mounting medium with DAPI. Fluorescence images were collected with a confocal microscope (Nikon 1000) at 200×. The fluorescence intensity from the cells in 3 images were averaged to assess peptide binding.

Competitive Inhibition Assay

Competitive inhibition of targeted peptide binding was evaluated by incubating the cells in culture with unconjugated (no FITC) peptide at concentrations of 100, 500, and 1000 µmol. Three fluorescence images were collected at 200× from each well of the chamber slide using the same gain and exposure time. Images selected for analysis met the following criteria: 1) 70-90% cell confluence, 2) away from the edge of each well, 3) low background binding on cell free area of slide, 4) No change in cellular morphology. The mean cell numbers under three 200× view were record to calculate the percentage of peptide binding cells. Quantification of the fluorescence intensities was done by NIH Image J software to calculate pixel value between each group under the same threshold. Differences in the mean fluorescence intensities were compared using a student's t test.

Human Tissue Specimen Collection

IRB approval was granted by the Stanford University Medical Center, the VA Palo Alto Health Care Systems, and El Camino Hospital. Human subjects with a history of Barrett's esophagus undergoing routine screening endoscopy were recruited for this study and informed consent was obtained. Subjects with coagulation abnormalities, or low tolerance for endoscopy were excluded from the study. Tissue specimens were collected using standard pinch biopsy from regions of endoscopically apparent Barrett's and squamous esophagus and duodenum mucosa. Histopathology was evaluated by two gastrointestinal pathologists in a blinded fashion according to common criteria (Goldblum, Mod Pathol 2003;16:316-24).

Targeted Peptide Binding on Esophageal Mucosa

The tissue specimens were placed immediately after excision in an Eppendorf tube containin PBS at 4° C. PBS and incubated with100 µmol of targeted peptide 'ASYNYDA' for 15 minutes at room temperature. After being washed three times with PBS at 4° C., the specimens were embedded in OCT freezing compound (Sakura finetek USA), cut in 6 µm sections, and placed onto Poly-D-lysine coated slides. The tissue specimens were fixed in acetone at 4° C. for 90 seconds, counterstained with DAPI, and mounted in Vectashield. An adjacent serial section of the specimen was cut and stained with H&E for routine histology and comparison.

For each specimen 10 serial section were screened under microscope. Three highest intensity fluorescence images were collected at 400× using the same gain and exposure time. Fluorescence intensities of images were quantified by NIH Image J software to calculate pixel value between each sample under the same threshold (40, 255). Differences in the mean fluorescence intensities between four tissue types were compared using a student's t test.

Example 1

Enrichment of Phage with Specific Binding to Seg-1 Cells

After two rounds of biopanning against 0E21 cells in the clearing step, ~93.5% of phage were removed from the original phage library. $1.3\times10^9$ left over phage were amplified once to reach $6\times10^{12}$pfu/ml. $2\times10^{11}$ of this phage were used for 3 rounds of Seg-1 binding. The recovered phage numbers after each round of Seg-1 binding were $2.5\times10^4$, $2.26\times10^3$ and $4.25\times10^2$. 48/425 individual phages were randomly selected and sequenced. Peptide sequences that appeared more than twice are listed in Table 1. BLAST search were carried out against the SWISSPORT database.

After two rounds of clearing panning, 93.5% of phage clone were cleared from original phage library. Then this "non-squamous" phage pool was incubated with Seg-1 cells in three rounds of continuous bio-panning. To avoid bias growth of phage clones, the eluted phage pool were not amplified between each round. Five peptide sequences were identified from 48 randomly selected phage clones out of a total of 425 phage clones in the third round binding elute. Peptide 17 expressing phage showed 10 and 5 times higher binding efficiency on Seg-1 cells when compared with none insert phage and the binding on QhTERT cells. Phage 17 has very specific binding on Seg-1 cell membrane in the following immunofluorescence assay. The binding efficiency difference of peptide 17 is the highest in our 5 phage candidates.

TABLE 1

| Peptide Sequences | | | | |
|---|---|---|---|---|
| Phage ID | Sequence | SEQ IN NO | Frequency | Example of homologous protein |
| 1, 7, 17, 23, 24, 28, 31, 32, 41 | ASYNYDA | SEQ ID NO: 01 | 9/48 | protocadherin 1 gamma 2, Danio rerio |
| 2, 19, 38 | AQLSTLA | SEQ ID NO: 02 | 3/48 | hCG1989245, Human |
| 3, 11 | QLMSADS | SEQ ID NO: 03 | 2/48 | CCT motif family protein, Tetrahymena thermophila |

TABLE 1-continued

Peptide Sequences

| Phage ID | Sequence | SEQ IN NO | Frequency | Example of homologous protein |
|---|---|---|---|---|
| 14, 27 | LPLHSLS | SEQ ID NO: 04 | 2/48 | Ig-like, group 1, Delftia acidovorans SPH-1 |
| 12, 33 | TGPTIQH | SEQ ID NO: 05 | 2/48 | Vang-like protein 2, Protein strabismus |

Example 2

Targeted Binding to Cells in Culture

Binding of the targeted peptide to esophageal adenocarcinoma (Seg-1) and Barrett's (QhTERT) cells in culture were performed. The phage expressing the targeted sequence 'ASYNYDA' showed 10 times higher recovery from Seg-1 cells compared to that using wild-type phage. Also, 'ASYNYDA' showed 5 times greater fluorescence intensity with Seg-1 than with QhTERT cells ($p<0.01$) binding affinity on Seg-1 cells which is the highest in 5 phage candidates. Phage 17 based cell immunofluorescence test also confirmed that it is binding on the plasma membrane of Seg-1 cells (FIG. 1 and FIG. 2) and very week binding on cytoplasm of QhTERT cells. None insert phage is not binding on Seg-1 cells. Peptide 17 was synthesized and conjugated with Fluorescence dye FITC. Scrambled peptide sequence 'YANSAYD' was synthesized also linked to fluorescein for use as a control. Peptide 17-FITC was binding on the plasma membrane of >90% Seg-1 cells (FIG. 3) and cytoplasm of 37% TE7, and 1% GIL hTERT(HGD) cells. Peptide 17 did not bind on OE21, QhTERT (normal Barrett's) cells. In addition, scrambled peptide-FITC also did not bind on any cells. It was also found that the binding of peptide 17-FITC could be inhibited by a 5 or 10 times higher concentration of unconjugated peptide 17 (FIG. 4. $P<0.01$).

Example 3

Targeted Binding to Esophageal Specimens

In the following example fresh biopsy tissues from human esophagus were used as binding targets. Esophageal specimens from n=16 human subjects, including n=13 with non-dysplastic intestinal metaplasia and n=3 with high-grade dysplasia, were evaluated for peptide targeted binding. Patients ranged in age from 42 to 86 years old (mean 65.75±11). Peptide 17 was binding in both normal Barrett's and dysplasia Barrett's tissues but not on duodenal mucosa, and adjacent normal esophagus mucosa. Confocal image verified that peptide is binding on plasma membrane. The binding pattern has much different between normal Barrett's and HGD tissues. In HGD tissue the binding site is a group of consecutive cells located in the mucosa and submucosa of esophageal. We have H&E staining on continuous sections, which shows that peptide is binding on dysplasia tissues. In normal Barrett's the binding site were sporadic separated cells in the surface of mucosa. The peptide-binding cell shows nuclear atypia and loss of nuclear polarity. These are similar to what is found in dysplasia tissues. Quantization analyze by NIH image J software shows peptide ASYNYDA has higher preferential bind on HGD than other tissues. $P<0.01$ (FIG. 5 and FIG. 6).

Example 4

In Vivo Molecular Imaging

Small Animal Models

In vivo molecular imaging has been performed in small animal models of esophageal neoplasia to localize binding by targeted peptides. A rigid endoscope for imaging the rat esophagus consists of a 9.5 Fr (3 mm) diameter rigid Hopkins II 0 deg telescope with a 11.5 cm working length (Karl Storz Veterinary Endoscopy, Goleta, Calif.). A 3 Fr (1 mm) diameter instrument channel is available to perform tissue biopsy. Fluorescence excitation light is produced with a 450 to 475 nm passband filter that can be manually placed into the optical path of a xenon (175 W) light source, and is delivered to the endoscope via a light guide.

Fluorescence images were collected with 510 nm barrier filter to block the excitation light, and detected with a color CCD camera. The molecular imaging studies were performed in the surgically-altered (EGJ) rats after 36 weeks. The rats were fasted overnight, anesthetized using inhaled isoflurane, and placed in the supine position. The extremities and incisors were restrained to prevent injury to the animal. The endoscope was inserted into the distal esophagus using ~1 to 2 ml of air injected through an instrument port to dilate the esophageal lumen. The FITC-labeled target peptide was topically administered through the instrument channel onto the distal esophagus in a 1 mL solution diluted in PBS at a concentration of 100 μM. After incubation for 5 minutes, excess peptide was rinsed off with tap water, and binding was evaluated by fluorescence. A white light endoscopic image of the distal esophagus reveals the presence of an esophageal adenocarcinoma present within a patch of Barrett's esophagus, as shown in FIG. 7, Panel a. Increased fluorescence intensity was observed at the site of the lesion with an average target-to-background ratio of 5±2, as shown in FIG. 7, Panel b. A complete examination usually lasts <2 minutes.

Clinical Imaging

A prototype endoscope was used to collect fluorescence images of peptide binding from human subjects with Barrett's esophagus and high-grade dysplasia using the target peptide labeled with FITC. With IRB approval and informed consent, human subjects with a history of Barrett's esophagus and biopsy proven high-grade dysplasia scheduled for endoscopic mucosal resection were recruited into the study. After esophageal intubation, a 10 second video was collected in the white light mode. Then, ~3 ml of peptide at a concentration of 10 μM was administered topically to the distal esophagus using a mist spray catheter. After 5 minutes for incubation, excess peptide was gently rinsed off with water, and another 10 second video was collected of the peptide targeted fluorescence image. The mucosa of the distal esophagus was then removed by endoscopic mucosal resection. Each video stream was exported into individual frames.

In FIG. 8, Panel a, a standard white light endoscopic image shows a 4 cm length of salmon pink mucosa consistent with endoscopically apparent Barrett's esophagus. No distinct architectural lesions can be appreciated. The targeted image, shown in FIG. 8, Panel b, reveals increased fluorescence intensity at a site (arrow) that was biopsied and evaluated as high-grade dysplasia on histopathology. The mean fluorescence intensities from 5 independent regions of HGD and non-dysplastic Barrett's metaplasia was found to have a target-to-background ratio of 1.52 in this set of images. Targeted biopsies were collected from sites suspicious for HGD, non-dysplastic Barrett's esophagus. The specimens were embedded in OCT media, cooled to 4° C., and cut into 10 µm horizontal sections on a cryostat.

The specimens were then evaluated for fluorescence on a tabletop confocal microscope, and an adjacent section was formalin fixed and stained with H&E for evaluation by two pathologists. FIG. 9 shows significant binding of the FITC-labeled peptide to the surface of cells (arrow) in Barrett's mucosa with high-grade dysplasia (Panel a), and minimal binding to Barrett's mucosa with no dysplasia (Panel b). Routine histology (H&E) of the corresponding images (Panels c and d) from adjacent frozen sections are also shown for purposes of comparison, magnification 400×.

Together, these examples show that the disclosed targeting peptides are useful in providing for localized delivery of therapeutic agents, such as a chemotherapeutic agent, early detection, risk stratification, monitoring of treatment therapy, and therapeutic intervention of cancer, such as esophageal adenocarcinoma.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A composition comprising a polypeptide comprising the sequence ASYNYDA (SEQ ID NO: 01), wherein the polypeptide is up to 50 amino acids in length.

2. The composition according to claim 1, wherein said polypeptide is coupled to at least one effector molecule.

3. The composition according to claim 2, wherein said effector molecule is a therapeutic agent, or a detectable molecule.

4. The composition according to claim 3, wherein said detectable molecule comprises a chelator, a complexed metal, an enriched isotope, radioactive material, a paramagnetic substance, an affinity label, a fluorescent label, a luminescent label, a PET-active substance or a SPECT-active substance.

5. The composition according to claim 3, wherein said detectable molecule is fluorescein or a fluorescein derivative.

6. The composition according to claim 3, wherein said detectable molecule is rhodamine or a rhodamine derivative.

7. The composition according to claim 3, wherein said therapeutic agent is a cytotoxic agent, a cytostatic agent, an immunomodulating agent, or a radiation emitting agent.

8. The composition according to claim 2, wherein said therapeutic agent is a chemotherapeutic agent.

9. A pharmaceutical composition comprising a polypeptide comprising the sequence ASYNYDA (SEQ ID NO: 01), coupled to a therapeutic agent, wherein the polypeptide is up to 50 amino acids in length.

10. The pharmaceutical composition according to claim 7, wherein said composition further comprises at least one of a pharmaceutically acceptable carrier, a pharmaceutically acceptable diluent, a pharmaceutically acceptable excipient and a pharmaceutically acceptable adjuvant.

11. The pharmaceutical composition according to claim 9, wherein said therapeutic agent is a cytotoxic agent, a cytostatic agent, an immunomodulating agent, or a radiation emitting agent.

12. The pharmaceutical composition according to claim 9, wherein said therapeutic agent is a chemotherapeutic agent.

13. A kit for detecting presence or absence of a tumor cell in a subject comprising: a composition comprising a polypeptide comprising the sequence ASYNYDA (SEQ ID NO: 01) coupled to a detectable molecule, wherein the polypeptide is up to 50 amino acids in length and wherein the polypeptide is capable of binding to a tumor cell.

14. The kit according to claim 13, wherein said detectable molecule comprises a chelator, a complexed metal, an enriched isotope, radioactive material, a paramagnetic substance, an affinity label, a fluorescent label, a luminescent label, a PET-active substance or a SPECT-active substance.

15. The kit according to claim 13, wherein said detectable molecule is fluorescein or a fluorescein derivative.

16. The kit according to claim 13, wherein said detectable molecule is rhodamine or a rhodamine derivative.

17. The kit according to claim 13, wherein said tumor cell is an adenocarcinoma cell.

18. The kit according to claim 13, wherein said adenocarcinoma cell is an esophageal cancer cell.

* * * * *

SEQUENCE LISTING

```
<160> NUMBER OF SEQ ID NOS: 6

<210> SEQ ID NO 1
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1

Ala Ser Tyr Asn Tyr Asp Ala
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 2

Ala Gln Leu Ser Thr Leu Ala
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 3

Gln Leu Met Ser Ala Asp Ser
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic Polypeptide
```

```
<400> SEQUENCE: 4

Leu Pro Leu His Ser Leu Ser
 1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 5

Thr Gly Pro Thr Ile Gln His
 1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 6

Tyr Ala Asn Ser Ala Tyr Asp
 1               5
```